United States Patent [19]

Allen

[11] Patent Number: 5,480,657
[45] Date of Patent: Jan. 2, 1996

[54] COMPOSITION COMPRISING CAFFEINE CHROMIUM AND FRUCTOSE FOR WEIGHT CONTROL AND USE THEREOF

[76] Inventor: Ann de Wees T. Allen, 2831 Gallows Rd., Ste. 206, Falls Church, Va. 22042

[21] Appl. No.: 141,604

[22] Filed: Oct. 27, 1993

[51] Int. Cl.[6] .......................... A61K 31/62; A61K 31/34; A61K 31/28; A61K 33/24
[52] U.S. Cl. .......................... 424/617; 514/262; 514/461; 514/505; 514/263; 514/264; 514/909
[58] Field of Search ...................................... 514/909, 263, 514/264, 262, 461, 505; 424/617

[56] References Cited

U.S. PATENT DOCUMENTS

| | | | |
|---|---|---|---|
| 4,923,855 | 5/1990 | Jensen | 514/188 |
| 4,954,492 | 9/1990 | Jensen | 514/188 |
| 5,013,752 | 5/1991 | Dobbins | 514/101 |
| 5,194,615 | 3/1993 | Jensen | 546/5 |

OTHER PUBLICATIONS

CA: 86:184308—Wulzner et al, Jun. 1977.
CA: 92:109625h—Wiesner et al, Mar. 1980.
Olin et al, "Comparative Retention/Absorption of Chromium (Cr) from Cr Chloride (CrCl), Cr Nicotinate (CrNic), and Cr Picolinate (CrPic) in a Rat Model," Abstract, Oct. 10, 1992, 33rd Annual Meeting of the American College of Nutrition.
Allen, "Chromium–Essential Fat Control Nutrient of the 90's," Feb. 1994 Research Summary, Bioavailable ChromeMate.
Allen, "Niacin–Bound Chromium Compounds Vary—ChromeMate's Oxygen–Coordinated Complex Found 18 Times More Potent," Fact Sheet #2, InterHealth Company, Oct. 5, 1992.
Allen, "UC Study Finds ChromeMate® More Bioavailable than Chromium Picolinate Chromium Chloride," Facts About Chromium Nutrition, Fact Sheet #3, InterHealth Company, Oct. 14, 1992.
Bukowiecki, "Regulation of Diet–Induced Thermogenesis in Brown Adipose Tissue," *Diet and Obesity*, 1988, pp. 71–85.
"Chromium in Human Nutrition," InterHealth Company, Jul. 21, 1992.

*Primary Examiner*—T. J. Criares
*Attorney, Agent, or Firm*—Burns, Doane, Swecker & Mathis

[57] ABSTRACT

A composition for the prevention or treatment of weight gain, e.g., obesity, said composition comprising caffeine, fructose and chromium in an effective amount to prevent or treat weight loss. Also disclosed is a method for the prevention or treatment of weight gain, e.g., obesity, by administering the composition of the present invention. The composition is conveniently administered as coffee, tea, cocoa or a carbonated beverage.

9 Claims, No Drawings

COMPOSITION COMPRISING CAFFEINE CHROMIUM AND FRUCTOSE FOR WEIGHT CONTROL AND USE THEREOF

BACKGROUND OF THE INVENTION

1. Field of the Invention

The present invention relates to a novel composition useful for weight control. The invention further relates and to the use of the novel composition for the prevention or treatment of weight gain in a mammalian organism in need of such prevention or treatment.

2. Related Art

The problems of weight control, in particular minimization of the accumulation of fat, has long been an issue of concern. While exercise is the main mechanism for achieving that goal, food or vitamin supplements have also been considered.

Conventional dieting employing caloric restriction has been shown to be unsuccessful for weight control. The human body was not meant to function on less than the minimal amount of calories. To do so results in fatigue, immune suppression, increased fat cell storage, depression, and eventual failure due to extreme hunger. In addition, statistics have shown that 95% of all persons who diet gain back most of the lost weight within one year.

Eating is the strongest urge known to the human race. It is rooted in the brain's genetic-survival program and cannot be ignored. Successful weight control depends on four important factors: sufficient caloric intake; balanced blood sugar levels; proper nutrient intake; and taste satisfaction with the food consumed. If any one of these factors is ignored, weight control is doomed to fail.

Moreover, the most successful methods of weight control function to reduce body fat. The elimination of body fat will result in dramatic weight control. For example, for every one pound of body fat lost, three pounds by weight are lost.

There remains a long-felt need in the art for a method of weight control that is convenient and yet can maintain its beneficial effects for a long period of time.

The present inventor has discovered a composition for weight control and method of using same that eliminates the above-described failure factors and functions to reduce body fat.

SUMMARY OF THE INVENTION

The present inventor has taken a different approach than the prior art for weight control. Surprisingly, it has been discovered that weight can be effectively controlled by reducing the body fat of a mammalian organism, e.g., human by administering the novel composition of matter of the present invention to a mammalian organism in need of a reduction or to maintain a reduction in body fat.

In general, it is an object of the present invention to provide a composition and method of using same for weight control that is an easy, safe and effective alternative to conventional dieting. The present invention thus provides a novel composition which is orally administered and method of using same for preventing or treating excess weight gain, e.g., obesity.

In particular, it is also an object of the present invention to provide a composition useful for weight control which comprises caffeine, chromium, and fruit sugar. Preferably, the composition comprises caffeine, niacin-bound chromium, and fruit sugar.

Further, it is an object of the present invention to administer the novel composition of the present invention in a manner which is safe and convenient. The product being consumed by the individual may be in the form of instant coffee, instant tea or a carbonated beverage.

DESCRIPTION OF THE PREFERRED EMBODIMENTS

The present inventor has found that the following five factors result in successful weight control: thermogenesis; low glycemia; decreased appetite control; increased energy via proper blood sugar balance; and chromium replenishment.

Thermogenesis is defined as the production of body heat by physiological processes. More specifically, it is the process of burning stored body fat. There are five pathways for stimulating thermogenesis in humans. The composition of the present invention accesses pathway number five, that is diet-induced thermogenesis. Diet-induced thermogenesis triggers a catalytic response which actually causes the body to burn its "fat fuel" at a higher rate. The composition of the present invention has surprisingly been found to thermogenically work on five separate levels, including diet-induced thermogenesis.

With respect to glycemia, everything we eat has an effect on our blood sugar. Foods which overly elevate blood sugar levels trigger an oversecretion of insulin, and insulin is a precursor of lipogenesis (fat storage). Aside from promoting fat storage, insulin peaks also cause low blood sugar which can set off eating binges. Thus, low glycemic food compositions which do not elevate blood sugar levels are desirable for weight control.

The compositions of the present invention have also been found to control appetite. False cravings for food are most often caused by low blood sugar. Humans need to eat every three hours to keep blood sugar levels properly balanced. Blood sugar levels account for energy as well as level of mental function. In the past, humans consumed small portions of food throughout the day. As a result, the human body continues to function more efficiently when fed every few hours. When one does not eat frequently enough, the result is tiredness, weakness, inability to focus and as a result of improper eating habits, weight gain eventually results. In our busy society, eating every few hours, however, is not possible. The composition of the present invention thus provides carbohydrates needed by the body to stop the blood sugar from plunging.

As previously stated, the compositions of the present invention comprise caffeine as one of its essential ingredients. Caffeine is an energy enhancer; however, caffeine also has an adverse effect on many people and can induce headaches or "the jitters", e g., a nervous sensation. The composition of the present invention thus also comprises fructose as a buffer or stabilizer to reduce the adverse effects of caffeine while retaining the energy enhancement properties of caffeine.

Caffeine, or 3,7-dihydro-1,3,7-trimethyl-1H- purine-2,6-dione, has the structural formula

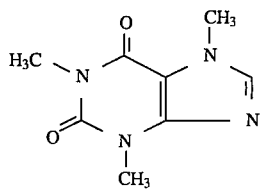

Caffeine is present in a number of natural foods such as coffee beans, tea leaves, cocoa beans and the like. The amount of caffeine actually derived from the products depends on the age of the natural product, the type of product, the geographic location from which the product was obtained, the period of time the product was allowed to brew, and the like. Caffeine is also found in canned or bottled beverages, especially carbonated soda.

The composition of the present invention is preferably administered in the form of coffee, tea, cocoa or carbonated soda. Most preferably, the composition of the present invention is administered in the form of instant coffee. The amount of instant coffee used to prepare one cup of coffee can range from approximately one to five teaspoons. Generally, two teaspoons of instant coffee are used to prepare one cup of coffee. Instant coffee and instant tea are especially useful mechanisms to administer the novel composition of the present invention since they are both relatively easy to measure and can be prepared from individual serving packets.

The amount of caffeine present in one serving of coffee, tea, cocoa or carbonated beverage can range from approximately 30 mg to 150 mg, preferably approximately 50 to 70 mg, most preferably approximately 65 mg. A serving generally ranges from six to twelve ounces depending on the beverage selected. These amounts of caffeine are the desired amounts present in the novel composition of the present invention.

A wide variety of other components, additives, flavoring agents and the like may be added to the present invention depending on the type of product or beverage to be administered. These other components are well-known to those of ordinary skill in the art and can readily be identified by referring to standard good or pharmaceutical reference texts, such as *Remington's Pharmaceutical Sciences*.

Coffee may be prepared, for instance, by adding approximately six ounces of hot or boiling water to approximately two teaspoons of instant coffee, which is then stirred. Iced coffee, hot tea, iced tea, hot cocoa and carbonated soda are also possible ways of administering the novel composition of the present invention.

The composition may be administered up to approximately eight times per day, however, it is generally taken two or three times per day.

Fructose is also present in the novel composition of the claimed invention. Fructose is commonly called "fruit sugar" because of its widespread occurrence free in fruits. Fructose may exist as either of two stereoisomers, designated as either D-fructose or L-fructose. The L-fructose form is preferred in the practice of the present invention. L-fructose is a ketohexose and its molecular formula is $C_6H_{12}O_6$. Its structural formula may be shown in the following ways:

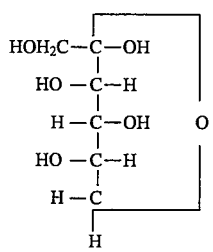

α-L-Fructopyranose

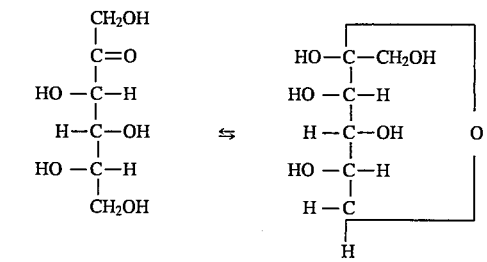

Keto-L-fructose       β-L-Fructopyranose

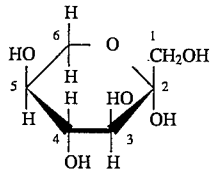

α-L-Fructopyranose
(perspective formula)

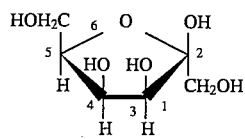

β-L-Fructofuranose
(perspective formula)

Fructose is used to supply energy. Fructose supplies relatively consistent energy levels with minimal or no stimulation of insulin production. Sugar (sucrose), honey, glucose and many common carbohydrates supply energy but they also stimulate insulin production. This causes rebound-tiredness and fat gains. By contrast, fructose which is used in the present composition remains in the intestinal tract for a longer period of time than regular sugars or carbohydrates. This provides for a type of time-released energy and therefore relatively consistent levels of energy production result.

Various sweeteners or sugars are known in the art. Monosaccharides, the simplest carbohydrates, are aldehydes or ketones having two or more hydroxyl groups, having the empirical formula $(CH_2O)_n$. Monosaccharides having an aldehyde functional group are known as aldoses while those having a ketone functional group are ketoses. A sugar having six carbon atoms is called a hexose. Common hexoses include fructose (a ketose) and glucose (an aldose). A disaccharide consists of two sugars joined by an O-glycosidic bond. Three highly abundant disaccharides are sucrose, lactose, and maltose. Sucrose (common table sugar) is obtained from cane or beet. The anomeric carbon atoms of a glucose and a fructose residue are in an α-glycosidic linkage in sucrose. Lactose, the disaccharide of milk, consists of galactose joined to glucose by a β1,4-glycosidic linkage. Maltose consists of two glucose units joined by an α1,4-glycosidic linkage.

Prior to recently developed concerns regarding body fat, sucrose and honey were the most commonly used sweeteners. These sugars however, have relatively high glycemic indexes and, therefore, cause an imbalance in insulin levels, thereby causing energy and mood swings, and stimulating cravings for sweets. As compared to other sweeteners, sugar and honey not only increase the urge for more sweets and carbohydrates, but also stimulate the pancreas to secrete 300% more insulin than, for example, fructose.

Because of the fat-storage effects of sucrose and honey, many food manufacturers concerned with health have switched to glucose and glucose polymers. Glucose is a crystalline sugar also found in fruits and honey. However, glucose releases 500% more insulin than fructose.

Fructose, which is used in the practice of the present invention, is a crystalline sugar found in fruits, fruit sugar, levulose and honey. It is the only natural sweetener which does not stimulate lipoprotein lipase, the gatekeeper for fat storage. More specifically, lipoprotein lipase is an enzyme responsible for clearing the milky plasma of alimentary hyperlipemia by hydrolyzing the fats. Unlike sucrose, honey and glucose, fructose holds the lowest glycemic index known. Therefore, it does not result in an imbalance of insulin levels, cause energy and mood swings, or stimulate cravings for sweets.

Although both fructose and glucose co-exist in nature, they elicit different effects in the body. To take advantage of the different biochemical responses of fructose and glucose, the two monosaccharides must be separated from the fruit in which they occur. This technique is well known in the art and is also inexpensive. Modern methods of separating various sugars from their original food sources allow the use of individual sugars in food and drink products. Problems arise, however, in the misuse and misapplication of the separated sugars, which is believed to result because of the failure to appreciate the differing glycemic index and glycemic responses elicited by the various sugars.

For example, an orange contains 50% sucrose, 30% fructose and 20% glucose. After fructose is separated from the other sugars in the orange, it has been found by the present inventor to be an ideal sweetener and carbohydrate. Currently, however, in most instances after the separation is complete, fructose is converted into high fructose corn syrup before being added to food products. This process results in a finished product which is 40% fructose and 60% glucose. The use of high fructose corn syrup thus does not result in the advantages of the present invention since its glycemic response is equal to sucrose due to the high percentage of glucose contained therein.

Further to the above-described benefits of using fructose instead of other sugars, fructose is an excellent fat-loss carbohydrate. In a controlled study, for example, it was found by the present inventor that people ingesting fructose as opposed to glucose could eat without caloric restriction. The fructose group chose to eat almost 500 calories per day less than the glucose group. This translates into a loss of 23 to 24 pounds of body fat per year without exercise or dieting. In this regard, the corresponding weight loss would be even more significant considering that the above-described 23 to 24 pounds is measured in terms of body fat, not total weight lost. When measuring total weight lost, the amount of body fat lost is only about ⅓ of the total weight lost. For example, if a person were to lose 10 pounds, typically the amount of actual body fat lost is ⅓ of that amount, which would be 3.33 pounds in this example. The remaining weight loss is attributable to loss of fluid and muscle tissue. For every pound of body fat burned, over one pound of water is produced as a chemical by-product. Muscle tissue loss can be reduced to near zero when losing body fat by keeping caloric intake high enough to sustain muscle mass while eating every three to four hours and reducing the amount of dietary fat and high glycemic foods.

The role of fructose as a thermogenic agent, a blood sugar balancer, and an ergogenic enhancer has thus been discovered by the present inventor. Such roles may be defined in terms of efficacy. In terms of thermogenesis, fructose is twice as effective as sucrose for burning extra calories. Diet-Induced-Thermogenesis is one of the dominant pathways used by the body to eliminate excess calories. In the treatment of blood sugar disorders, fructose is frequently prescribed by physicians in controlling reactive hypoglycemia and diabetes. As an ergogenic tool, fructose increases endurance and stamina in athletes and may be used to overcome a major hurdle in athletic performance. For example, overstimulation of insulin production which results in a brief "high" followed by a long and drastic energy "low" can be avoided. Controlling insulin is key in determining athletic performance in events of short or long duration. Using the correct sugars and carbohydrates to derive the optimum insulin reaction relative to a specific athletic event is one of the primary pathways to maximize human performance.

The present inventor has surprisingly found, however, that simply ingesting fructose as opposed to glucose does not result in an increase in weight loss. In the study performed by the present inventor three control groups were used. The first group consumed fructose, the second group consumed sucrose, while the third group consumed plain water. Surprisingly, the water-drinking group craved and ate more food than did the fructose consuming group.

Too much sugar of any type, even fructose, is capable of being converted to fat. Fructose, however, has the least proclivity towards fat storage as compared to any other sugar or carbohydrate known. Excess carbohydrate consumption in any form as defined by ingestion of carbohydrates unused by the body may eventually lead to elevated serum cholesterol and triglycerides. As previously discussed, however, the present invention has now found that the rise in serum lipids associated with excess sugar/carbohydrate consumption can be greatly reduced, if not eliminated, by adding specific components to fructose when it is in its raw crystalline form.

The amount of fructose in the composition of the present invention is an effective amount to achieve the desired effect of the present invention, i.e., to work along with the other components present in order to prevent or treat unnecessary weight gain in a mammalian organism, e.g., humans. The amount of sugar generally ranges from approximately 2 to 20 grams per serving, preferably approximately 3 to 12 grams per serving, and more preferably approximately 5 grams per serving. As noted above, a serving usually represents about six to twelve ounces.

Some chemical compounds have been found to be important not for their direct influence on weight control, but rather as complements to or synergists for other compounds which stimulate weight control. Chromium is one such compound. Chromium, which is present in the novel composition of the present invention, has been found to be a beneficial supplement for athletes. For example, it has been speculated that chromium losses are twice as high on a workout day versus a non-workout day. Chromium has thus been added to the fructose formulations of the present invention.

Chromium, like iron, copper and zinc, is one of 16 essential trace minerals the human body needs to function properly. For athletes, for example, chromium may be the most important essential trace metal. In its biologically active form, chromium helps insulin metabolize fat, convert protein to muscle and convert sugar into energy in vivo. In fact, chromium-activated insulin increases the amount of glucose available for energy production nearly twenty-fold. By increasing the efficiency of glucose utilization, chromium expands the body's energy-producing capacity beyond the normal limits. For example, during exercise the point at which muscle burn occurs can be greatly extended by increasing the amount of chromium in the blood-stream.

In addition, chromium is the "master" nutrient for controlling blood sugar. Chromium in vivo helps overcome sugar cravings, a problem many people experience, for example, due to diets high in sugars and refined carbohydrates. This essential trace mineral also helps level out the highs and lows of a high carbohydrate diet, promoting a steady stream of available glucose for continuous, prolonged energy. Chromium also acts to control blood lipids, lowering harmful LDL cholesterol and increasing beneficial HDL cholesterol.

Chromium deficiency results in various adverse effects in humans. For example, a lack of sufficient amount of chromium can impair insulin function, inhibit muscle development and decrease energy production. In addition, such a deficiency can lead to type II diabetes and even heart disease. U.S. government studies show that the diets of nine out of ten Americans are deficient in chromium, containing less than the minimum safe and adequate amount established by the National Research Council (50–200 micrograms/day). This problem is even worse, for example, for athletes, diabetics, pregnant and lactating women and the elderly. For example, in athletes, their nutritional requirements are higher due to increased energy demands due to the fact that chromium is rapidly depleted during workouts. For example, following a strenuous workout, chromium loss has been shown to increase five times the normal rate. Moreover, a consumption of sugars and refined carbohydrates, a major part of many athletes' diets, can increase chromium loss up to 300%. Although chromium naturally occurs in many foods, processing removes up to 80% of that chromium. Still further, less than 2% of the chromium from most food sources is actually absorbed. For dieters who have restricted their calories and reduced their nutritional intake, even less chromium is actually absorbed. Thus, it is difficult to obtain sufficient chromium even if foods high in chromium content are eaten.

Foods rich in biologically active chromium, which is the form that activates insulin action, are Brewer's yeast, black pepper, liver and wheat germ. However, even Brewer's yeast, the richest known source of biologically active chromium in nature, contains only a few micrograms of chromium per gram, less than 10% of which is in the biologically active form. Higher potencies of biologically active chromium, for example, up to 200 micrograms, are thus desirable.

Niacin-bound chromium has been identified as the biologically active chromium ingredient in Brewer's yeast by Dr. Walter Mertz, former director of the USDA Human Nutrition Research Center and discoverer of biologically active chromium. Niacin-bound chromium is available under the Tradename of CHROMEMATE®. A description of CHROMEMATE® may be found in U.S. Pat. Nos. 4,923855, 4,954,492 and 5,194,615, which patents are hereby incorporated by reference in their entirety. Independent university studies have now found that the oxygen-coordinated chromium-niacin complex is the most bioactive of other known niacin-bound chromium, being over eighteen times more bioactive.

Chromium has been found to be a beneficial supplement for athletes. For example, it has been speculated that chromium losses are twice as high on a workout day versus a non-workout day. Chromium has thus been added to the fructose formulations of the present invention.

Chromium, in its biologically active form, helps insulin metabolize fat and convert food into energy. Chromium-activated insulin increases the amount of glucose available for energy nearly twenty-fold. This results in optimum energy output. Chromium is also the "master" nutrient for controlling blood sugar which controls sugar cravings. Curbing the cravings for sweets is essential if weight loss is the goal. U.S. government studies have shown that nine out of ten Americans are deficient in chromium, which is one reason many Americans are overweight. Chromium was previously available in the food supply; however, processing presently removes up to 80% of the chromium in foods. Since less than 2% of the chromium from most foods is actually absorbed, it is easy to see why the vast majority of people are chromium deficient. Different forms of chromium have been researched by the present inventor. It has been found that the preferred biologically acceptable form is niacin-bound chromium, called chromium polynicotinate.

The strong potentiation of insulin in vitro has been found to depend upon the coordination of nicotinic acid to chromium. This has been shown by the ineffectiveness of other pyridine carboxylic acid derivatives, such as picolinic acid, as ligands. Unlike the niacin isomer picolinic acid, niacin binds with chromium only at either the nitrogen or carboxylic acid position. In addition, chromium nicotinate tends to form positively charged complexes in vivo. Researchers believe that this fact may help explain why chromium nicotinate is absorbed and/or retained better than other chromium complexes. Studies have shown that red blood cells absorb positively charged chromium complexes better than neutral or negatively charged complexes. By comparison, for example, chromium picolinate is a neutral complex, while chromium chloride tends to form neutral or negatively charged complexes in vivo. The preferred chromium nicotinate of the present invention is thus more bioavailable than both chromium picolinate and chromium chloride, both of which are recognized as potentially useful forms of inorganic chromium.

As previously discussed supra, Brewer's yeast typically contains only 2 micrograms chromium per gram of yeast, of which only a fraction is in the biologically active O-coordinated form, and attempts to biosynthetically increase the concentration of glucose tolerance factor chromium in Brewer's yeast have met with limited success. However, any form of chromium including chromium picolinate, chromium chloride and the like are useful in the practice of the present invention. Niacin-bound chromium is preferred in the practice of the present invention.

The chromium is present in an amount of approximately 5 mcg to 500 mcg per serving. Preferably, the chromium is present in an amount of between about 10 mcg to about 100 mcg per serving, more preferably the chromium is present in an amount of approximately 50 mcg per serving, wherein a serving is approximately six to twelve ounces.

Optionally, other components may also be present in the composition of the present invention including sodium, potassium, dietary fiber, calcium, magnesium, vitamin A, vitamin C, thiamine, riboflavin, niacin, iron and the like.

Research has shown that elevated serum cholesterol and triglycerides associated with excess sugar/carbohydrate consumption is related to a specific mineral deficiency. Thus, a mineral agent may be added to the novel composition of the present invention.

In order to further illustrate the present invention, the following specific examples are given, it being understood that the same are intended as illustrative and in nowise limitative.

EXAMPLES

Example 1

A study was conducted to determine the glycemic response to various sugars. The study included fifteen volunteer subjects who ingested 10 grams of a specific sugar, as set forth in Table I below. The sugar was diluted with water to equal one fluid cup. The response was quantified by plasma glucose (PG, mg/dl) via blood samples drawn at one-half hour intervals following ingestion of placebo or non-placebo sample. Plasma samples were drawn with fasting after 30 minutes, 60 minutes, 90 minutes, 120 minutes, and 240 minutes. A total of six samples were obtained per subject. Insulin elevation was then recorded as set forth in Table I below.

| SUGAR | INSULIN SPILLOVER |
|---|---|
| Sucrose | Positive |
| Fructose | Negative |
| Glucose | Positive |
| Dextrose | Positive |
| Corn Syrup | Unacceptable |
| Sorbitol | Unacceptable |
| Mannitol | Unacceptable |
| Xylitol | Positive |
| Maltodextrin | Positive |
| Glucose Polymers | Positive |
| High Fructose Corn Syrup | Positive |
| Grape Sugar | Positive |
| Honey | Positive |
| Brown Sugar | Positive |

The above sugars were designated for insulin spillover according to their calorigenicity and insulinogenicity. Both calorigenicity and insulinogenicity of a sweetener is recognized as being involved in the accumulation of excess body fat. Insulin stimulates the activity of adipose tissue lipoprotein lipase, which as previously discussed is the key enzyme regulating the uptake and storage of blood triglycerides as body fat.

As can be seen from Table I, the only acceptable sugar which met acceptable guidelines for calorigenicity and insulinogenicity was fructose. Fructose was the only sugar for which no insulin elevation was noted and which was clinically acceptable. The clinical implications of fructose in diabetic and non-diabetic subjects when used as the primary sweetener in foods and liquids can thus be seen. Though some of the noninsulin-requiring sugars tested (sorbitol, mannitol and xylitol) did not adversely affect glucose response, these sugars were unacceptable as they caused diarrhea. Moreover, these sugars did not act as buffers (non-pH buffer) to the adrenal-exhaustive responses to caffeine. Nor did they maintain blood sugar levels or provide energy as did fructose. The sorbitol, mannitol and xylitol were thus designated as unacceptable for a composition to defray or satiate hunger, provide energy, maintain balanced blood sugar levels, or buffer caffeine response.

Example 2

An instant coffee having a serving size of two teaspoons (6 grams) and 21 calories having the following nutritional information:

| | |
|---|---|
| Sodium | 1/200 gram |
| Potassium | 36 mg |
| Total Carbohydrate | 5 g |
| Dietary Fiber | (less than 1 gram) |
| Fruit Sugar | 5 g |
| Calcium | 6 mg |
| Magnesium | 5 mg |
| Niacin-bound chromium | 100 mcg |
| Caffeine | 65 mg | was added to six ounces boiling water and stirred. It was swallowed two to three times per day. The coffee may be enjoyed with meals or a cup of coffee may be taken 30 minutes before meals or two hours after meals.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A composition for the prevention or treatment of weight gain, said composition comprising approximately 30 to 150 mg of caffeine, approximately 2 to 20 grams fructose and approximately 5 mcg to 500 mcg chromium, per serving.

2. The composition of claim 1 wherein the amount of caffeine is about 65 mg, the amount of fructose is about 5 grams and the amount of chromium is about 50 mcg per serving.

3. The composition of claim 1 wherein the composition is contained in an instant coffee product.

4. The composition of claim 1 wherein the composition is contained in an instant tea product.

5. The composition of claim 1 wherein the composition is contained in a cocoa product.

6. The composition of claim 1 wherein the composition is contained in a soda beverage.

7. A method for treating weight gain, said method comprising administering the composition of claim 1 to a mammalian organism in need of such treatment.

8. A composition comprising about 65 mg caffeine, about 5 grams fructose and about 50 mcg chromium.

9. An instant coffee composition comprising about 65 mg caffeine, about 5 grams fructose and about 50 mcg chromium.

* * * * *